Figure 1:
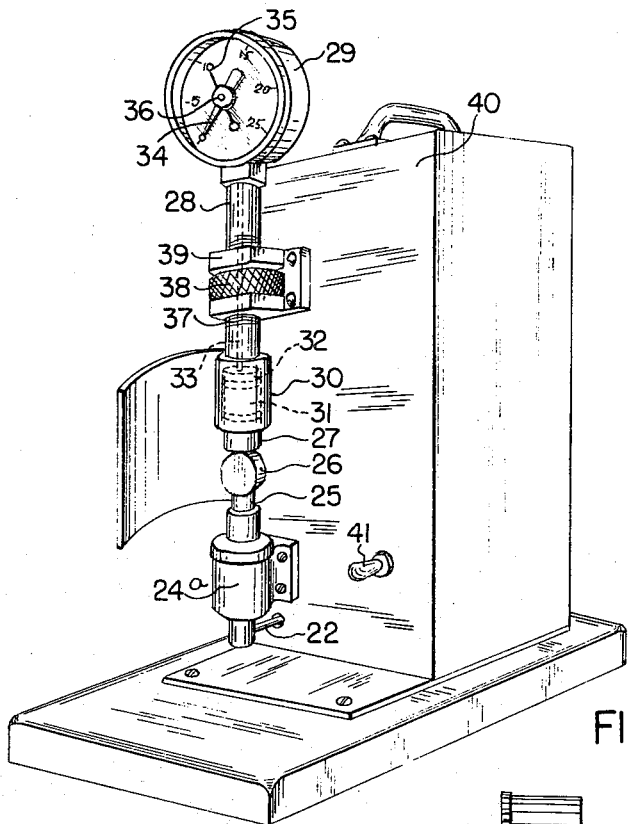

United States Patent [19]
Wilhelm, Jr.

[11] 3,943,757
[45] Mar. 16, 1976

[54] TABLET HARDNESS TESTER AND METHOD OF TESTING

[75] Inventor: John W. Wilhelm, Jr., Moreland Hills, Ohio

[73] Assignee: Skidmore-Wilhelm Mfg. Co., Cleveland, Ohio

[22] Filed: Jan. 30, 1975

[21] Appl. No.: 545,598

[52] U.S. Cl. ................................................. 73/78
[51] Int. Cl.² ........................................... G01N 3/10
[58] Field of Search ............................... 73/78, 81

[56] References Cited
UNITED STATES PATENTS

| | | | |
|---|---|---|---|
| 1,192,670 | 7/1916 | Moore et al. | 73/81 |
| 2,209,020 | 7/1940 | Billman et al. | 73/81 |
| 2,975,630 | 3/1961 | Michel | 73/78 |
| 3,478,568 | 11/1969 | Borgersen | 73/81 |

FOREIGN PATENTS OR APPLICATIONS

| | | | |
|---|---|---|---|
| 2,059,811 | 4/1972 | Germany | 73/78 |

Primary Examiner—James J. Gill
Assistant Examiner—Anthony V. Ciarlante
Attorney, Agent, or Firm—Baldwin, Egan, Walling & Fetzer

[57] ABSTRACT

A method of testing the hardness of a circular tablet is presented and comprises holding the tablet on edge between two members respectively on opposite sides of the tablet, transmitting a controlled pressure to the tablet through one of the members, transmitting from said tablet through the other of said members to a pressure gauge and recording the maximum pressure on the gauge up to the moment that the tablet breaks. Apparatus is presented including a frame holding a source of pressure fluid, communicating said fluid to a pressure cylinder mounted beneath a tablet to be tested which is supported in a vertical position on edge, having the fluid pressure cylinder beneath the tablet and having a plunger in contact with the upper side of the tablet and connected with a load cell and pressure transmitting means with a pressure indicating gauge, all of this above the tablet.

1 Claim, 2 Drawing Figures

U.S. Patent   March 16, 1976   3,943,757

TABLET HARDNESS TESTER AND METHOD OF TESTING

BACKGROUND OF THE INVENTION

Remington's "Practice of Pharmacy" states: "A good finished uncoated tablet will be firm enough to just break between the second and third fingers when using the thumb finger as a fulcrum." Attempts have been made to carry out such a test of a molded tablet hardness, but these have not given sufficiently reliable and reproduceable results to be depended upon. One vention as shown and described in connection with the drawings of this application, but the source of pressure fluid was led from the upper end of the machine over to a common communicating line between an upper pressure gauge and leading downwardly through a pressure cylinder to a plunger resting on the top of the tablet to be tested, which in turn rested on a fixed anvil below the tablet. This previous machine was not wholly reliable because of friction in the parts transmitting the fluid pressure downwardly to the top of the tablet and also because at times higher pressure was transmitted to the gauge than actually was necessary to break the tablet.

The present invention provides means for lightly holding a tablet to be tested vertically on edge between an upper and a lower member, together with means for transmitting a controlled fluid pressure to an air cylinder effective to raise the lower member upwardly to press against the tablet, together with a pressure-transmitting train above the tablet including a plunger in contact with the top of the tablet, a load cell in contact with that plunger, and pressure transmission means between the load cell and the pressure indicating gauge, all of this above the tablet being tested, together with means for adjusting the position of the parts to accommodate tablets of different diameter for testing, means for controlling the source of fluid pressure, etc., to obtain an efficient testing apparatus.

An object of the present invention is to provide method and means for testing the hardness of a molded tablet by holding the tablet vertically on edge with pressure transmitting members lightly clamping the tablet between them, and then means for transmitting a controlled fluid pressure against the tablet on one side, and transmitting the pressure coming through the tablet to a recording pressure gauge, whereby when the tablet breaks, no further transmission of pressure is possible and the gauge gives an accurate record of the maximum pressure used to disintegrate the tablet.

Other objects and advantages of this invention will be apparent from the drawings and description and the essential features thereof will be set forth in the appended claims.

Figure 2:
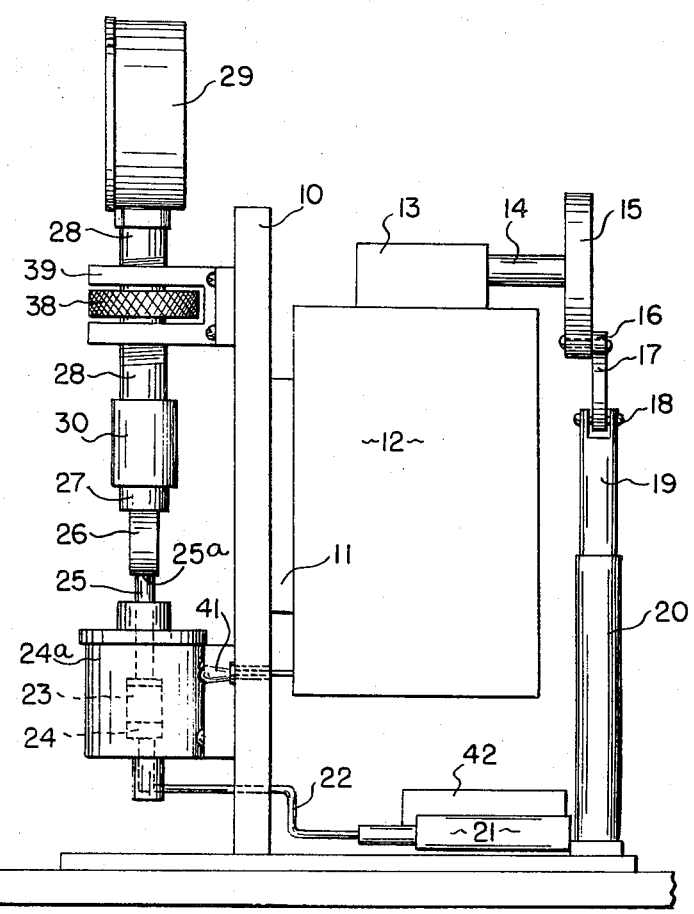

In the drawings,

FIG. 1 is a perspective view of an apparatus for performing the objects of the present invention; while FIG. 2 is a side elevation of the same, slightly enlarged, taken along the right-hand side of FIG. 1.

Referring to the drawings, a frame 10 supports at 11 a housing 12 which encloses an electrical gear motor, which through gear box 13 drives an output shaft 14 to which is rigidly attached a cam wheel 15. At one point on the cam wheel, a pivot 16 connects a link 17 which in turn is connected by pivot 18 to a piston 19 which reciprocates in a cylinder 20. The piston 19 has a small leather cup at its lower edge and as the motor rotates the cam 15 and oscillates the piston 19, it builds up air pressure at the lower end of cylinder 20. This communicates through a suitable opening to a check valve 21 which permits passage of air only from right to left as seen in FIG. 2. The pressure fluid then communicates through conduit 22 with the lower face of a piston 23 which is reciprocatable in an air cylinder 24. The piston is rigidly connected with a piston rod 25 which extends out of the top of the air cylinder, through suitable seals, and terminates in an arcuate tablet seat 25a.

The tablet for testing is indicated at 26 in a vertical position endwise between the seat 25a and a plunger 27 which is the lowest member in a column 28 providing a pressure transmitting mechanism from the plunger 27 to the pressure indicating gauge 29 at the top of the column. The plunger 27 is sealed in a load cell 30 which includes a piston 31 sealed in a suitable cylinder wall in the cell and transmitting pressure from below to a filling of hydraulic fluid which extends from the upper face of the piston in the cylinder chamber 32 through an upwardly extending pressure transmitting line 33 which extends centrally through the column 28 to the top thereof where it communicates with the gauge 29. This gauge is of a well known character which includes a pressure movable needle 34 and preferably a maximum indicating needle 35 which is carried by the needle 34 to the maximum indicated pressure when a tablet is being tested. A resetting knob 36 permits the operator to return the needle 35 to the zero position of needle 34, as seen in FIG. 1, for each successive tablet testing operation.

Means is provided for adjusting the distance between piston rod 25 and the plunger 27 so as to accommodate tablets of different size diameters. The means here shown includes a thread 37 on the column 28 which is threaded into an adjusting nut 38 which is vertically held in a bracket 39 attached to the housing 40 which surrounds the parts shown at the right-hand side of FIG. 2, this housing being omitted from FIG. 1 to show the structure in a better manner. By rotating the ring 38 the column 28 may be moved upward and downward as necessary to lightly grip the tablet 26 between the members 25 and 27 before a test takes place.

A toggle switch actuator is shown at 41 which has suitable connections to start and stop the motor in the housing 12.

A solenoid operated release valve is indicated at 42 adapted, when actuated, to connect the line 22 with atmosphere to release the pressure in the cylinder 24 at the close of a tablet testing operation.

In operation of the device, a tablet 26 to be tested is placed vertically on edge as shown in the drawings and adjusts the column 28 by means of the adjustment ring 38 to cause the members 27 and 25 to lightly grip the tablet in the position shown. The operator then manipulates the toggle switch at 41 causing the motor in the housing 12 to operate so as to thereby reciprocate the piston 19 in the cylinder 20 to build up air pressure passing through 21 and 22 to the air cylinder 24. Compressed air then moves the piston 23 and the piston rod 25 upward until it breaks the pill or tablet 26. During the build up of pressure beneath the piston 23 which is transmitted through the piston rod 25 to the lower side of tablet 26, this pressure is transmitted to the plunger 27 and through the load cell 30 and the hydraulic fluid in cylinder 32 and transmission line 33 up to the pressure indicating gauge 29. The indicating needle 34 will gradually move in a clockwise manner as seen in FIG. 1 past the indicating readings on the dial of the gauge 29 carrying the maximum indicating needle 35 with it. At the moment the tablet 26 breaks, no further pressure can be transmitted upwardly to the gauge 29 and, therefore, the maximum indicating needle 35 indicates the true pressure at which the tablet was broken.

This testing system allows for any differences in the air cylinder 24 since the gauge 29 measures the pressure after the cylinder, instead of before the cylinder, as in previous devices described herein. The area of the small hydraulic load cell 30 and the consequent frictional effects will be constant from one unit to another. This means that the gauge 29 can be calibrated in a meaningful area to indicate the breaking stress of the tested tablet 26.

Since the load cell 30 has a known area, this pressure may be converted, if desired, to unit of force capable of indicating the breaking load on the tested tablet or pill.

The source of pressure fluid is shown as a piston motor 19, 20 driven by a motor in housing 12. This piston motor could be manually driven by a lever, or the source might be a controlled supply of compressed air.

The tablet is shown and claimed tested vertically on edge. It could be tested horizontally edgewise.

What is claimed is:

1. A molded tablet hardness tester comprising a frame, a source of pressure fluid mounted on said frame, means for controlling said source, a fluid pressure cylinder mounted in a low position on said frame with its axis vertical, a piston reciprocatably mounted in said cylinder with a piston rod extending vertically upwardly therefrom and terminating in an arcuate seat, a pressure fluid line communicating between said source and said cylinder on the lower side of said piston, a check valve in said line permitting flow only toward said cylinder, a normally closed pressure release valve in said line downstream from said check valve, means for optionally opening said pressure relief valve, a pressure transmitting assembly mounted on said frame above said piston rod and vertically in line with said cylinder axis, said assembly including in pressure transmitting relation, from the bottom upwardly, a plunger adapted to have its lower end in contact with a tablet to be tested and its upper end sealed in a load cell and said pressure transmitting assembly including a piston sealed in said cell, a hollow column extending upwardly from said cell, and an upwardly extending pressure transmitting line in said column and in communication with the upper face of said last named piston and filled with hydraulic fluid, and a pressure indicating gauge mounted on said column and connected to said pressure transmitting line and having a resettable maximum register needle, and said assembly mounting including means for vertically adjusting said assembly vertically relative to said frame including a rotatable adjusting wheel having a threaded engagement with said column, a fixed bracket on said frame restricting vertical movement of said wheel, whereby to clamp a tablet for testing lightly between said first named piston rod and said plunger by rotation of said wheel, whereby with a tablet so clamped said fluid pressure source may be actuated to pressurize said cylinder below said first named piston to cause said pressure to be transmitted through said tablet and to be registered on said gauge until said tablet breaks.

* * * * *